United States Patent
Chew et al.

(10) Patent No.: US 7,094,422 B2
(45) Date of Patent: *Aug. 22, 2006

(54) TOPICAL DELIVERY OF ANTIFUNGAL AGENTS

(75) Inventors: Nora Yat Knork Chew, Melbourne (AU); Barry Leonard Reed, Strathmore (AU); Timothy Matthias Morgan, Carlton North (AU); Barrie Charles Finnin, Glen Iris (AU)

(73) Assignee: Acrux DDS PTY Ltd., Victoria (AU)

( * ) Notice: Subject to any disclaimer, the term of this patent is extended or adjusted under 35 U.S.C. 154(b) by 344 days.

This patent is subject to a terminal disclaimer.

(21) Appl. No.: 10/644,085

(22) Filed: Aug. 20, 2003

(65) Prior Publication Data

US 2004/0081684 A1 Apr. 29, 2004

Related U.S. Application Data

(60) Continuation-in-part of application No. 09/910,780, filed on Jul. 24, 2001, now Pat. No. 6,818,226, which is a division of application No. 09/125,436, filed as application No. PCT/AU07/00091 on Feb. 19, 1997, now Pat. No. 6,299,900.

(30) Foreign Application Priority Data

Feb. 19, 1996 (AU) ............................................. PN8144

(51) Int. Cl.
*A61F 13/02* (2006.01)

(52) U.S. Cl. ...................................... 424/448; 424/449

(58) Field of Classification Search ................. 424/448, 424/449

See application file for complete search history.

(56) References Cited

U.S. PATENT DOCUMENTS

| | | | |
|---|---|---|---|
| 3,598,122 | A | 8/1971 | Zaffaroni |
| 3,598,123 | A | 8/1971 | Zaffaroni |
| 3,742,951 | A | 7/1973 | Zaffaroni |

(Continued)

FOREIGN PATENT DOCUMENTS

| | | |
|---|---|---|
| AU | 30258/89 | 9/1989 |
| AU | 49984/1990 | 9/1989 |
| AU | 91413/91 | 6/1992 |
| DE | 43 34 553 | 4/1995 |
| EP | 189 861 | 8/1986 |
| EP | 0 552 405 A1 | 7/1993 |
| EP | 0 608 322 B1 | 7/1998 |
| JP | 61-268631 | 11/1986 |
| WO | WO 92/19271 | 11/1992 |
| WO | WO 96/30000 | 10/1996 |

OTHER PUBLICATIONS

R.J. Feldmann et al., "Percutaneous Penetration of 14C Hydrocortisone in Man", Arch Derm, vol. 94:649–651, (1966).

(Continued)

*Primary Examiner*—Shelley A. Dodson
*Assistant Examiner*—Konata M. George
(74) *Attorney, Agent, or Firm*—Foley & Lardner LLP

(57) ABSTRACT

The present invention provides a topical drug delivery system which comprises: a therapeutically effective amount of an antifungal agent; at least one dermal penetration enhancer, which is a safe skin-tolerant ester sunscreen ester; and a volatile liquid. The invention also provides a method for administering at least one systemic acting antifungal agent to an animal which comprises applying an effective amount of the antifungal agent in the form of the drug delivery system of the present invention.

16 Claims, 1 Drawing Sheet

U.S. PATENT DOCUMENTS

Figure 1:
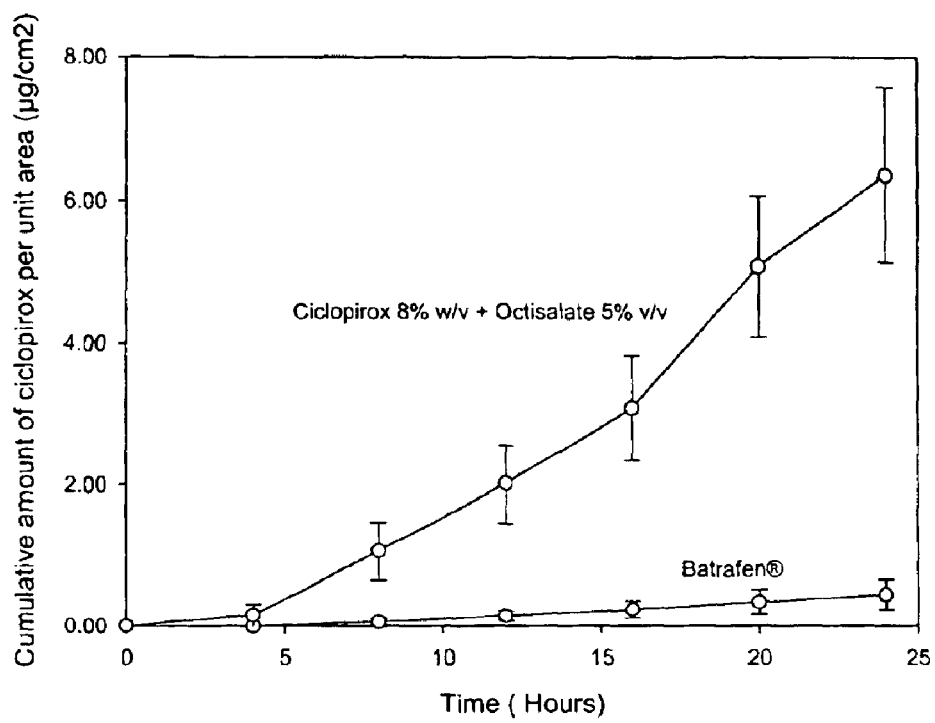

| | | | |
|---|---|---|---|
| 3,814,097 | A | 6/1974 | Ganderton et al. |
| 3,921,636 | A | 11/1975 | Zaffaroni |
| 3,989,816 | A | 11/1976 | Rajadhyaksha |
| 3,993,072 | A | 11/1976 | Zaffaroni |
| 3,993,073 | A | 11/1976 | Zaffaroni |
| 3,996,934 | A | 12/1976 | Zaffaroni |
| 4,031,894 | A | 6/1977 | Urquhart et al. |
| 4,060,084 | A | 11/1977 | Chandrasekaran et al. |
| 4,069,307 | A | 1/1978 | Higuchi et al. |
| 4,077,407 | A | 3/1978 | Theeuwes et al. |
| 4,201,211 | A | 5/1980 | Chandrasekaran et al. |
| 4,230,105 | A | 10/1980 | Harwood |
| 4,292,299 | A | 9/1981 | Suzuki et al. |
| 4,292,303 | A | 9/1981 | Keith et al. |
| 4,299,826 | A | 11/1981 | Luedders |
| 4,310,511 | A | 1/1982 | Holick |
| 4,440,777 | A | 4/1984 | Zupan |
| 4,557,934 | A | 12/1985 | Cooper |
| 4,663,157 | A | 5/1987 | Brock |
| 4,699,779 | A | 10/1987 | Palinczar |
| 4,704,406 | A | 11/1987 | Stanislaus et al. |
| 4,820,724 | A | 4/1989 | Nimni |
| 4,820,742 | A | 4/1989 | Alexander et al. |
| 4,938,951 | A | 7/1990 | Leung et al. |
| 4,941,880 | A | 7/1990 | Burns |
| 4,946,671 | A | 8/1990 | Bissett et al. |
| 4,954,487 | A | 9/1990 | Cooper et al. |
| 5,023,085 | A | 6/1991 | Francoeur et al. |
| 5,034,386 | A | 7/1991 | Peck et al. |
| 5,036,100 | A | 7/1991 | Deboeck et al. |
| 5,082,656 | A | 1/1992 | Hui et al. |
| 5,082,866 | A | 1/1992 | Wong et al. |
| 5,122,519 | A | 6/1992 | Ritter |
| 5,256,647 | A | 10/1993 | Minaskanian et al. |
| 5,323,769 | A | 6/1994 | Bommannan et al. |
| 5,449,519 | A | 9/1995 | Wolf et al. |
| 5,474,783 | A | 12/1995 | Miranda et al. |
| 5,487,898 | A | 1/1996 | Lu et al. |
| 5,573,754 | A | 11/1996 | Kulkarni et al. |
| 5,679,374 | A | 10/1997 | Franchon et al. |
| 5,804,168 | A | 9/1998 | Murad |
| 6,299,600 | B1 * | 10/2001 | Masaoka et al. ............ 604/118 |
| 6,299,900 | B1 | 10/2001 | Reed et al. |

OTHER PUBLICATIONS

M.F. Coldman et al., "Enhancement of Percutaneous Absorption by the Use of Volatile: Nonvolatile Systems and Vehicles", Journal of Pharmaceutical Sciences, vol. 58(9): 1098–1102, (1969).

P.P. Bhatt et al., "Finite Dose Transport of Drugs in Liquid Formulations Through Stratum Corneum: Analytical Solution to a Diffusion Model", International Journal of Pharmaceutics, Elsevier Science Publishers B.V. vol. 50:197–203, (1989).

Bucks et al., Percutaneous Absorption of Hydroquinone in Humans: Effect of 1–Dodecylazacloheptan–2–One (Azone) and the 2 Ethylhexyl Ester of 4–(Dimethylamino) Benzoic Acid (Escalol 507), Journal of Toxicology and Evironmental Health, 24:279–289 (1988).

Physicians' Desk Reference (49 Ed.) 1995, pp. 1151–1152, Medical Economics Company, Inc. Montvale N.J.

Khabir Ahmed "US Physicians and WHO plead for aid to Afghanistan", The Lancet, vol. 357, Jun. 2001, pp. 1769.

William M. Chambers et al., "Terbinafine–Induced hepatic dysfunction", European Journal of Gastroenterology & Hepatology 2001, vol. 13, No. 9, pp. 1115–1118.

D.T. Roberts, "Onychomycosis: current treatment and future challenges", British Journal of Dermatology, 1999, 141 (Suppl. 56):1–4.

A. Tosti et al., "Relapses of Onychomycosis after Succesful Treatment with Systemic Antifungals: A Three Year Follow Up", Dermatology 1998: 197: 162–166.

Daniele Debruyne et al., "Pharmacokinetics of Antifungal Agents in Onychomycoses", Clin. Pharmacokinet 2001: 40:(6): 441–472.

Claus Seebacher et al., "A Multicenter, Open–Label Study of the Efficacy and Safety of Ciciopirox Nail Lacquer Solution 8% for the Treatment of Onychomycosis in Patients with Diabetes", Efficacy and Safety of Ciclopirox, vol. 68, Aug. 2001, pp. 17–22.

Roderick James Hay et al., "Risk/benefit ratio of modern antifungal therapy: Focus on hepatic reactions", Journal of the American Academy of Dermatology, Jul. 1993, pp. S50–S54.

D.T. Roberts, "Oral Terbinafine (Lamisil®) in the Treatment of Fungal Infections of the Skin and Nails", Dermatology 1997, 194 (supp 1):37–39.

Harvey Lemont et al., "Terbinafine–Associated Taste Disturbance with Normal Taste Threshold Scores", Journal of the American Podiatric Medical Association, pp. 540–541.

M. Zaug et al., "Amorolfine in the treatment of onychomycoses and dermatomycoses (an overview)", Clinical and Experimental Dermatology 1992, 17 (Suppl. 1): 61–70.

R.J. Hay et al., "Tioconazole nail solution—an open study of its efficacy in onychomycosis", Clinical and Experimental Dermatology (1985) 10, 111–115.

Barrie C. Finnin et al., "Transdermal Penetration Enhancers: Applications, Limitations, and Potential", Journal Pharmaceutical Sciences, vol. 88, No. 10, Oct. 1999, pp. 955–958.

Aditya K. Gupta et al., "Ciclopirox nail lacquer solution 8% in the 21$^{st}$ century" J. Am. Acad Dermatol, Oct. 2000, pp. S96–S102.

* cited by examiner

TOPICAL DELIVERY OF ANTIFUNGAL AGENTS

This application is a continuation-in-part of U.S. patent application Ser. No. 09/910,780, filed Jul. 24, 2001 now U.S. Pat. No. 6,818,226 which is a divisional of U.S. patent Ser. No. 09/125,436 now U.S. Pat. No. 6,299,900, filed Dec. 18, 1998 as the U.S. national stage application of application PCT/AU97/00091, filed Feb. 19, 1977. The entire contents of each of U.S. patent application Ser. No. 09/910,780, U.S. Pat. No. 6,299,900, and PCT application PCT/AU97/00091 are incorporated herein by reference, and priority to each is claimed under 35 U.S.C. § 119 and/or § 120.

FIELD OF THE INVENTION

The present invention relates to topical drug delivery. More specifically, the invention relates to a topical absorption/penetration enhancing agent for use in the delivery of antifungal agents and antifungal agent derivatives to an animal, including a human. The invention also relates to a system for the non-occlusive delivery to an animal of antifungal agents and antifungal agent derivatives across a dermal surface of the animal.

BACKGROUND OF THE INVENTION

There is a constant need for methods for the safe and effective administration of physiologically active agents, such as antifungal agents. For many medications it is important that the administration regime is as simple and non-invasive as possible in order to maintain a high level of compliance by a patient. Oral administration is one administration regime that is commonly used because it is a relatively simple regime to follow. However, the oral administration route is also complicated because of complications associated with gastrointestinal irritation and with drug metabolism in the liver. Adverse effects consisted of, liver damage, hepatic dysfunction, congestive heart failure (Ahmad S R et al, Lancet. 2001 Jun. 2; 357(9270):1766–7; Hay R J, J Am Acad Dermatol. 1993 Jul. 29(1):S50–4.; Chambers W M, Eur J Gastroenterol Hepatol. 2001 Sep. 13(9):1115–8), transient taste disturbance (Lemont H, Sabo M., J Am Podiatr Med Assoc. November-December 2001; 91(10):540–1), gastro disturbance and rashes (Roberts D T., Dermatology. 1997;194 Suppl 1:37–9.). Poor responsiveness and relapse of the oral therapy is also common (Roberts D T, Br J Dermatol (1999), 141 (suppl 5–6), 1–4; Tosti A et al, Dermatol (1998) 197, 162–166). As a number of the antifungal agents are potent inhibitors of cytochrome P450 (CYP) enzymes, drug-drug interactions may affect therapeutic outcome (Debruyne D, Coquerel A., Clin Pharmacokinet. 2001;40(6):441–72).

Administration of physiologically active agents through the skin ('topical drug delivery') has received increased attention because it not only provides a relatively simple dosage regime but it also provides a relatively slow and controlled route for release of a physiologically active agent into the local tissue. Topically administered ciclopirox (Batrafen®, Aventis Pharma Ltd, Auckland, New Zealand) (Seebacher C, Nietsch K H, Ulbricht H M., Cutis. August 2001;68(2 Suppl):17–22; Gupta A K, Baran R, J Am Acad Dermatol. October 2000;43(4 Suppl):S96–102.), amorolfine (Loceryl®, Gladerma, Amersham, UK) (Zaug M et al, Clin Exp Dermatol, (1992) 17 (Sup 1): 61–70) and tioconazole (Trosyl®, Pfizer, Sandwich, UK) (Hay R J et al, Clin Exp Dermatol, (1985) 10:111–115) have demonstrated efficacy in treating nail fungal infection (onychomyosis) to some extent. Onychomycosis is known to affect the nail plate and nail bed. Topical agents capable of lateral diffusion into the infected areas would be beneficial. However, topical drug delivery is complicated by the fact that the skin behaves as a natural barrier and therefore transport of agents through the skin is a complex mechanism.

Structurally, the skin consists of two principle parts, a relatively thin outermost layer (the 'epidermis') and a thicker inner region (the 'dermis'). The outermost layer of the epidermis (the 'stratum corneum') consists of flattened dead cells which are filled with keratin. The region between the flattened dead cells of the stratum corneum is filled with lipids which form lamellar phases that are responsible for the natural barrier properties of the skin.

For effective local delivery of a physiologically active agent that is applied to the surface of the skin ('topical application'), the agent must be partitioned firstly from the vehicle into the stratum corneum, it must typically then be diffused within the stratum corneum before being partitioned from the stratum corneum to the local tissues including the viable epidermis, dermis, subcutis and appendageal.

To overcome some of the problems with topical delivery that are associated with transport across the dermal layers ('percutaneous absorption'), physiologically active agents are commonly formulated with incorporation of one or more dermal penetration enhancers (Finnin and Morgan, J. Pharm. Sci., Vol 88, No. 10, October 1999, pp. 755–758) which are often lipophilic chemicals that readily partition into the stratum corneum whereupon they exert their effects on improving the transport of drugs across the skin barrier.

There is a need for improved compositions for topical delivery of antifungal agents.

SUMMARY OF THE INVENTION

According to the present invention there is provided a topical drug delivery system which comprises:
a. a therapeutically effective amount of an antifungal agent;
b. at least one dermal penetration enhancer, which is a safe skin-tolerant ester sunscreen of formula (I):

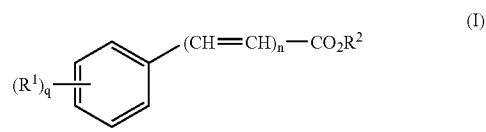

wherein
$R^1$ is hydrogen, lower alkyl, lower alkoxy, halide, hydroxy or $NR^3R^4$;
$R^2$ is a $C_8$ to $C_{18}$ alkyl,
$R^3$ and $R^4$ are each independently hydrogen, lower alkyl or $R^3$ and $R^4$ together with the nitrogen atom to which they are attached form a 5- or 6-membered heterocyclic ring;
n is 0 or 1, and
q is 1 or 2,
wherein when n is 0 and $R^1$ is $NR^3 R^4$, then $NR^3 R^4$ is para-substituted and wherein said dermal penetration enhancer is present in an amount of from about 10 to about 10,000 wt % based on the weight of the antifungal agent; and c. at least one volatile liquid.

In addition to providing improved percutaneous absorption efficiency, the composition of the invention may also provide lower irritancy than some other more occlusive delivery systems such as transdermal patches, because the composition is non-occlusive to the skin.

More preferably the dermal penetration enhancer is selected from the group consisting of a $C_8$ to $C_{18}$ alkyl para-aminobenzoate, $C_8$ to $C_{18}$ alkyl dimethyl-para-aminobenzoate, $C_8$ to $C_{18}$ alkyl cinnamate, $C_8$ to $C_{18}$ alkyl methoxycinnamate or $C_8$ to $C_{18}$ alkyl salicylate. Most preferably the dermal penetration enhancer is octyl salicylate, octyl dimethyl para-aminobenzoate or octyl para-methoxycinnamate (Padimate O).

The drug delivery systems according to the invention may comprise one or more antifungal agents together with the penetration enhancer incorporated into a dosage form for topical application to the skin of animals.

Suitable dosage forms include creams, lotions, gels, ointments, mousses, sprays, aerosols, or any one of a variety of transdermal devices for use in the continuous administration of systematically active drugs by absorption through the skin. Some examples of suitable vehicles are given in U.S. Pat. Nos. 3,598,122, 3,598,123, 3,742,951, 3,814,097, 3,921,636, 3,993,072, 3,993,073, 3,996,934, 4,031,894, 4,060,084, 4,069,307, 4,201,211, 4,230,105, 4,292,299, 4,292,303, 5,323,769, 5,023,085, 5,474,783, 4,941,880 and 4,077,407. These disclosures are thus hereby incorporated herein by reference.

Optionally the drug delivery system may contain pharmaceutical compounding agents, such as one or more thickening agents such as cellulosic thickening agents, ethylcellulose, hydroxypropyl cellulose, hydroxypropyl methylcellulose, povidone, polyacrylic acids such as carbopol, Sepigel® (polyacrylamide/isoparaffin/laureth-7), the Gantrez® series of polymethyl vinyl ether/maleic anhydride copolymers such as the butyl ester of PVM/MA copolymer Gantrez® A425, and any thickening agent known in the art that has good compatibility with the volatile liquid and enhancers of the present invention.

Preferred antifungal agents of the present invention include at least one of amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc pyrithione and sodium pyrithione. Further preferred antifungal agents include at least one of butenafine, butoconazole, clioquinol, itraconazole, lanoconazole, neticonazole, tioconazole, terconazole, ciclopirox olamine or pharmaceutically acceptable salts or derivatives of any one of the aforementioned.

In one preferred form of the invention the drug delivery system comprises on a weight basis from about 0.1 to about 10% of the antifungal agent, from about 0.1 to 10% of the at least one dermal penetration enhancer and from about 40 to 99.8% of a volatile liquid. In another preferred form the volatile liquid is ethanol, isopropanol, ethyl acetate or mixture thereof in the range of about 80 to 98%.

In another preferred form of the invention the drug delivery system comprises, on a weight basis, from about 3 to 8% of an antifungal agent, from about 1 to 5% of the dermal penetration enhancer, from about 45 to 90% ethanol, isopropanol, ethyl acetate or mixture thereof, 0.1 to 10% water; and optionally 0.5 to 5% of a thickening agent.

Whilst it is preferred that the antifungal agent and penetration enhancer be delivered by simultaneous administration, the penetration enhancer may be applied before or after the application of the antifungal agent, if desired.

The present invention also provides a method for administering at least one systemic or locally acting antifungal agent to an animal which comprises applying an effective amount of the antifungal agent in the form of the drug delivery system of the present invention.

Preferably the animal is a human but the invention also extends to the treatment of non-human animals.

Preferably the drug delivery system is not supersaturated with respect to the antifungal agent. As the volatile liquid of the drug delivery system evaporates, the resulting non-volatile composition is rapidly driven into the dermal surface. It is possible that as the volatile liquid evaporates, the non-volatile dermal penetration enhancer becomes supersaturated with respect to the antifungal agent. However, it is preferred that any supersaturation does not occur before transport of the resulting non-volatile composition across the epidermal surface has occurred.

It is most desirable that, after application of the drug delivery system, the volatile component of the delivery system evaporates and the area of skin to which the drug delivery system was applied becomes touch-dry. Preferably said area of skin becomes touch-dry within 10 minutes, more preferably within 3 minutes, most preferably within 1 minute.

The group of dermal penetration enhancing ester sunscreen compounds of the present invention are particularly suitable for topical delivery antifungal agents through the skin of an animal. These dermal penetration enhancing compounds are of low toxicity to the skin and are excellent promoters of percutaneous absorption.

Preferred volatile liquids of the present invention include safe skin-tolerant solvents such as ethanol, ethyl acetate and isopropanol. An aerosol propellant, such as dimethyl ether, may constitute a volatile liquid for the purpose of the present invention.

Surprisingly the group of dermal penetration compounds identified enhance the absorption of antifungal agents through the skin while avoiding the significant pharmacological disadvantages and toxicities of prior art enhancers. Additionally, the group of compounds of the invention surprisingly exhibit appreciable penetration into and substantivity for the outer layers of the skin, namely the stratum corneum which has previously presented a formidable barrier to percutaneous drug absorption.

In drug delivery systems according to the present invention a pharmaceutical compounding agent, co-solvent, surfactant, emulsifier, antioxidant, preservative, stabiliser, diluent or a mixture of two or more of said components may be incorporated in these systems as is appropriate to the particular route of administration and dosage form. The amount and type of components used should be compatible with the dermal penetration enhancers of this invention as well as with the antifungal agent. A co-solvent or other standard adjuvant, such as a surfactant, may be required to maintain the antifungal agent in solution or suspension at the desired concentration.

The pharmaceutical compounding agents can include paraffin oils, esters such as isopropyl myristate, ethanol, silicone oils and vegetable oils. These are preferably used in the range 1 to 50%. Surfactants such as ethoxylated fatty alcohols, glycerol mono stearate, phosphate esters, and other commonly used emulsifiers and surfactants preferably in the range of 0.1 to 10% may be used, as may be preservatives such as hydroxybenzoate esters for preservation of the compound preferably in amounts of 0.01% to 0.5%. Typical co-solvents and adjuvants may be ethyl alcohol, isopropyl alcohol, acetone, dimethyl ether and glycol ethers such as diethylene glycol mono ethyl ether. These may be used in amounts of 1 to 50%.

Because of the effect of the penetration enhancer of the invention, the dosage of the antifungal agent may often be less than that conventionally used. It is proposed that, a dosage near the lower end of the useful range of the particular antifungal agent may be employed initially and increased as indicated from the observed response if necessary.

The concentration of antifungal agent used in the drug delivery system will depend on its properties and may be equivalent to that normally utilised for the particular antifungal agent in conventional formulations. Both the amount antifungal agent and the amount of penetration enhancer will be influenced by the type of effect desired.

Where it is desired to achieve higher local concentration of an antifungal agent, proportionately higher concentrations of the enhancer of the invention may be required in the transdermal drug delivery system of the present invention, and the amount of antifungal agent included in the composition should be sufficient to provide the tissue level desired.

The concentration of absorption/penetration enhancer may be in the range from 10–10,000 weight percent of absorption/penetration enhancer based upon the weight of antifungal agent. The ratio of penetration enhancer to antifungal agent may vary considerably and will be governed as much as anything, by the pharmacological results that are required to be achieved. In principle, it is desirable that as little absorption enhancer as possible is used. On the other hand, for some antifungal agents, it may well be that the upper range of 10,000% by weight will be required. It is preferred that the penetration enhancer and antifungal agent are in approximately equal proportions.

A particular advantage of the drug delivery system of the present invention is that patient compliance is improved as the system does not occlude the skin. As a result local irritation and allergic sensitization problems arising from prolonged exposure of the skin to both the delivery system of occlusive transdermal patch devices and the adhesive used to affix these patches to the skin are reduced.

The following definitions apply through this description and the claims which follow.

The term "comprise" or variations such as "comprising" and "comprises" will be understood to imply the inclusion of a stated integer or group of integers but not the exclusion of any other integer or group of integers.

The terms "topical" and "transdermal" are used herein in the broadest sense to refer to being able to pass through unbroken skin.

The term "dermal penetration enhancer" is used herein in its broadest sense to refer to an agent which improves the rate of percutaneous transport of active agents across the skin or use and delivery of active agents to organisms such as animals, whether it be for local application or systemic delivery.

The term "non-occlusive" is used herein in its broadest sense to refer to not trapping or closing the skin to the atmosphere by means of a patch device, fixed reservoir, application chamber, tape, bandage, sticking plaster, or the like which remains on the skin at the site of application for a prolonged length of time.

The term "stratum corneum" is used herein in its broadest sense to refer to the outer layer of the skin, which is comprised of (approximately 15) layers of terminally differentiated keratinocytes made primarily of the proteinaceous material keratin arranged in a 'brick and mortar' fashion with the mortar being comprised of a lipid matrix made primarily from cholesterol, ceramides and long chain fatty acids. The stratum corneum creates the rate-limiting barrier for diffusion of the active agent across the skin.

The term "skin-depot" is used herein in its broadest sense to refer to a reservoir or deposit of active agent and dermal penetration enhancer within the stratum corneum, whether it be intra-cellular (within keratinocytes) or inter-cellular.

The term "volatile:non-volatile liquid vehicle" is used in the art to refer to a liquid pharmaceutical vehicle comprising a volatile liquid mixed with a non-volatile liquid vehicle, such as a dermal penetration enhancer. A system or vehicle comprising a volatile liquid mixed with a non-volatile dermal penetration enhancer when described herein is used in its broadest sense to include those systems known as volatile:non-volatile liquid vehicles.

Alkyl and alkoxy groups referred to herein may be either straight chain or branched. The term "lower alkyl" means alkyl groups containing from 1 to 5 carbon atoms. The term lower alkoxy has a similar meaning. The term "long chain alkyl" means alkyl groups containing from 5 to 18 carbon atoms, more preferably 6 to 18 carbon atoms. The term "halide" means fluoride, chloride, bromide or iodide. The term "heterocyclic ring" is herein defined to mean a ring of carbon atoms containing at least one hetero atom, and further the ring may be saturated or unsaturated to any allowable degree.

The term "sunscreen" is used herein in its broadest sense to refer to a chemical agent capable of filtering out ultra-violet light.

The drug delivery system of the present invention enables a wide range of antifungal agents to be delivered through the skin to achieve a desired systemic effect. The drug delivery system preferably comprises the antifungal agent intimately mixed with a non-volatile dermal penetration enhancer and a volatile liquid. Where the drug delivery system is applied to the skin, the antifungal agent and non-volatile liquid are thermodynamically driven into the skin as the volatile liquid evaporates. Once within the skin the non-volatile liquid may either disrupt the lipid matrix and/or act as a solubilizer to allow an enhanced penetration rate of the antifungal agent through the skin and into the subject being treated. In this way, the dermal penetration enhancer acts as a vehicle and many systemic active antifungal agents are able to be percutaneously administered to an animal.

It is believed that the non-volatile dermal penetration enhancer is readily absorbed into the stratum corneum in sufficient quantities to form a reservoir or depot of the dermal penetration enhancer within the stratum corneum. The dermal penetration enhancer also contains the antifungal agent to be administered and as the dermal penetration enhancer crosses into the skin to form the skin-depot, the antifungal agent contained therein is transported through the skin and contained within the depot. These depots are believed to form within the lipid matrix of the stratum corneum wherein the lipid matrix creates a rate-limiting barrier for diffusion of the antifungal agent across the skin and allows the dermally administered antifungal agent to be topically released over a period of time, usually up to 24 hours.

Once the volatile liquid of the drug delivery system has evaporated, driving the mixture of non-volatile dermal penetration enhancer and antifungal agent into the stratum corneum, the outer surface of the skin is then substantially free of antifungal agent and non-volatile dermal penetration enhancer. Normal touching, wearing of clothes, rinsing or even washing of the skin will not, to any significant extent, affect delivery of the antifungal agent or displace either the antifungal agent or the non-volatile dermal penetration enhancer, once the volatile liquid has evaporated.

This is in contrast to prior-art systems where supersaturated solutions are used to increase the rate of drug permeation across the skin. Such supersaturated solutions are susceptible of ready precipitation and require stabilization, such as with polymers, or protection from external surfaces or objects which may effect nucleation.

The rate of absorption of the antifungal agent via the stratum corneum is increased by the non-volatile dermal penetration enhancer. The antifungal agent may be dissolved or suspended in the dermal penetration enhancer at the time when it is being transported from the surface of the skin and into the stratum corneum. The performance of the dermal penetration enhancer to deliver a desired antifungal agent varies with differences in both the nature of the dermal penetration enhancer and the antifungal agent. It is understood that different dermal penetration enhancers may need to be selected to be appropriate for delivery of various antifungal agents.

Diseases or conditions that may be treated by using the drug delivery system and methods of the present invention include, but are not limited to, fungal infections due to the expanding understanding of the benefit of antifungal agents for such purposes.

The drug delivery system of the present invention may be applied to the skin by means of an aerosol, spray, pump-pack, brush, swab, or other applicator for the dosing of topical liquids.

DETAILED DESCRIPTION OF THE INVENTION

The invention will now be described with reference to the following examples and accompanying FIGURE. The examples and figure are not to be construed as limiting the invention in any way. They are included to further illustrate the present invention and advantages thereof.

In the accompanying FIGURE:

FIG. 1 Shows the cumulative amount of ciclopirox olamine penetrating across human epidermis ($\mu g/cm^2$) versus time (hours) for the topical solution composition 1A with or without the dermal penetration enhancer, octyl salicylate. Error bars represent Standard Error of the Mean (SEM).

In the examples, the effectiveness of the penetration enhancers is illustrated by measuring the skin penetration of formulations of a number of antifungal agents with the dermal penetration enhancers. Also, the skin penetration of antifungal agents was measured with Batrafen® (Aventis Pharma Ltd, Auckland, New Zealand), which serve as the control formulation. The comparisons made generally consisted of measuring the relative penetration through human epidermal skin of the various formulations. In every case, those formulations which contained the dermal penetration enhancers delivered more of the antifungal agent through the skin than did the corresponding control formulation.

EXAMPLE 1

| Topical spray compositions | | | |
|---|---|---|---|
| Composition 1A (Batrafen ®) | | Composition 1B | |
| Component | Amount | Component | Amount |
| Ciclopirox olamine | 8% w/v | Ciclopirox olamine | 8% w/v |
| 2-propanol | Unknown | Octyl salicylate | 5% v/v |
| Ethyl acetate | Unknown | Aqueous ethanol (95% v/v) | 45% v/v |
| Copolymer or methylvinylether and maleic acid monobutyl ester | Unknown | Ethyl acetate | 45% v/v |
| | | Water | 5% v/v |

As shown in FIG. 1 the addition of the safe sunscreen ester dermal penetration enhancer, octyl salicylate, surprisingly caused a marked 5 to 6-fold increase in the transdermal delivery of ciclopirox across the skin (p<0.01).

The diffusion experiments were performed using human epidermis as the model membrane. These experiments were performed over 24 h with stainless steel, flow-through diffusion cells based on those previously described, (Cooper, E. R. J. Pharm. Sci. 1984, 73, 1153–1156.) except that the cell was modified to increase the diffusional area to 1.0 cm². A finite dose of 5 µl/cm² of the formulation was applied to the diffusion cell and left uncovered for the diffusion of the experiment. A piece of stainless steel wire mesh was placed directly below the skin in the receptor chamber of the diffusion cell to maintain a turbulent flow of receptor solution below the skin. The diffusion cells were maintained at a flow rate of approximately 1.0 mL/cm²/h by a microcassette peristaltic pump (Watson Marlow 505S, UK). The cells were kept at 32±0.5° C. by a heater bar and the samples are collected into appropriately sized plastic vials on an automated fraction collector (Isco Retriever II, Lincoln, NE) at specified intervals. The receptor solution (water with 0.002% w/v sodium azide) maintained sink conditions beneath the skin.

Samples were analysed for ciclopirox olamine directly by UV spectrophotometer at the absorption wavelength of 300 nm.

While the invention has been described in detail and with reference to a specific example thereof, it will be apparent to one skilled in the art that various changes and modifications can be made therein without departing from the spirit and scope thereof.

We claim:

1. A topical drug delivery system which comprises:
   a. a therapeutically effective amount of an antifungal agent;
   b. at least one dermal penetration enhancer, which is a safe skin-tolerant ester sunscreen of formula (I):

$$(R^1)_q\text{-}\underset{}{\bigodot}\text{-}(CH=CH)_n\text{-}CO_2R^2 \quad (I)$$

wherein $R^1$ is hydrogen, lower alkyl, lower alkoxy, halide, hydroxy or $NR^3R^4$;

$R^2$ is a $C_8$ to $C_{18}$ alkyl, $R^3$ and $R^4$ are each independently hydrogen, lower alkyl or $R^3$ and $R^4$ together with the nitrogen atom to which they are attached form a 5- or 6-membered heterocyclic ring;

n is 0 or 1, and q is 1 or 2, wherein when n is 0 and $R^1$ is $NR^3 R^4$, then $NR^3 R^4$ is para-substituted; and wherein said dermal penetration enhancer is present in an amount of from about 10 to about 10,000 wt % based on the weight of the antifungal agent; and c. a volatile liquid.

2. A topical drug delivery system according to claim 1, wherein the dermal penetration enhancer is octyl salicylate.

3. A topical drug delivery system according to claim 2, wherein the antifungal agent is selected from the list consisting of amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc pyrithione and sodium pyrithione.

4. A topical drug delivery system according to claim 2, wherein the antifungal agent is selected from the list consisting of butenafine, butoconazole, clioquinol, itraconazole, lanoconazole, neticonazole, tioconazole, terconazole, or pharmaceutically acceptable salts or derivatives of any one of the aforementioned antifungal agents.

5. A topical drug delivery system according to claim 2, wherein the antifungal agent is ciclopirox olamine.

6. A transdermal drug delivery system according to claim 1, wherein the volatile liquid is ethanol, isopropanol or mixture thereof.

7. A transdermal drug delivery system according to claim 6 comprising on a weight basis:
   a. from about 0.1 to about 10% of the antifungal agent;
   b. from about 1 to 10% of the dermal penetration enhancer; and
   c. from about 40 to 99.8% ethanol, isopropanol or mixture thereof.

8. A topical drug delivery system according to claim 6 which comprises on a weight basis:
   a. from about 2 to about 8% of the antifungal agent;
   b. from about 1 to about 10% of the dermal penetration enhancer; and
   c. from about 40 to 98% ethanol, isopropanol, ethyl acetate or mixture thereof; and
   d. from about 0.5 to 10% water.

9. A topical drug delivery system according to claim 6 which comprises on a weight basis:
   a. from about 3 to about 8% ciclopirox olamine;
   b. from about 1 to about 10% octyl salicylate;
   c. from about 40 to 95% ethanol and 40–95% Ethyl Acetate; and
   d. from about 1 to 5% water.

10. A topical drug delivery system according to claim 6 which comprises on a weight basis:
    a. from about 3 to about 8% ciclopirox olamine;
    b. from about 1 to about 5% octyl salicylate;
    c. from about 45 to 95% ethanol, isopropanol, ethyl acetate or mixture thereof;
    d. from about 1 to about 5% water; and
    e. from about 0.5 to about 5% of a thickening agent.

11. A method for administering at least one local acting antifungal agent to an animal which comprises applying an effective amount of the antifungal agent in the form of a drug delivery system according to claim 1.

12. A method according to claim 11, wherein the antifungal agent is ciclopirox olamine.

13. A method according to claim 12, wherein the composition is applied to the skin of the human or animal covering a delivery surface area between 10 and 800 cm$^2$.

14. A method according to claim 12 wherein the composition is applied to the skin of the human or animal covering a delivery surface area between 10 and 400 cm$^2$.

15. A method according to claim 12, wherein the composition is applied to the skin of the human or animal covering a delivery surface area between 10 and 200 cm$^2$.

16. A method according to claim 15, wherein the composition is applied using a fixed or variable metered dose applicator.

* * * * *